US00PP15156P2

(12) United States Plant Patent
Olesen et al.

(10) Patent No.: US PP15,156 P2
(45) Date of Patent: Sep. 21, 2004

(54) ***CLEMATIS VITICELLA* PLANT NAMED 'EVIPO024'**

(50) Latin Name: *Clematis viticella*
Varietal Denomination: EVIpo024

(75) Inventors: Mogens N. Olesen, Fredensborg (DK); Raymond J. Evison, St. Sampsons (GB)

(73) Assignee: Poulsen Roser A/S, Fredensborg (DK)

( * ) Notice: Subject to any disclaimer, the term of this patent is extended or adjusted under 35 U.S.C. 154(b) by 4 days.

(21) Appl. No.: 10/640,794

(22) Filed: Aug. 13, 2003

(51) Int. Cl.[7] ..... A01H 5/00
(52) U.S. Cl. ..... Plt./228
(58) Field of Search ..... Plt./228

*Primary Examiner*—Kent Bell

(57) ABSTRACT

A new Clematis cultivar which is well suited to propagation in glasshouses. With a tall growth habit, profuse, purple flowers, and spring and autumn flowering.

The variety successfully propagates from softwood cuttings and is suitable for cultivation in commercial glasshouses. This new and distinct variety has shown to be uniform and stable in the resulting generations from propagation.

1 Drawing Sheet

Botanical classification: *Clematis viticella.*
Variety denomination: 'EVIpo024'.
Commercial classification: Early and late flowering cultivar.

SUMMARY OF THE INVENTION/DISCOVERY

The present invention constitutes a new and distinct variety of Clematis which originated from a controlled crossing between 'Burma Star', unpatented, and 'H.F. Young', un-patented. The two parents were crossed and the resulting seed was planted in a controlled environment. The new variety is named "EVIpo024."

'EVIpo024' may be distinguished from the pollen parent H.F. Young from its flower color. While 'H.F. Young' is light purple, 'EVIpo024' is darker, Purple Group 79D in color.

'EVIpo024' may be distinguished from the seed parent 'Burma Star' by the following characteristics. 'Burma Star' has darker colored filaments and stamens than 'EVIpo024' 'Burma Star' has a lighter purple flower color than 'EVIpo024'.

The objective of the hybridization of this Clematis variety for commercial glasshouse and nursery culture was to create a new and distinct variety with unique qualities that this variety has:

1. Purple flowers.
2. Abundance of paler toned anthers gives flower light colored center.
3. Very free flowering, good repeat flowering.
4. Extremely compact habit.
5. Flowers well as a young plant.
6. Good choice for small container use.

These qualities required improvement in Clematis varieties that were in commercial cultivation and the objectives have been substantially achieved in the new variety, as evidenced by the unique combination of characteristics that are present in "EVIpo024" which distinguish it from all other varieties of which we are aware.

The seeds from the hybridization were germinated and evaluations were conducted of the resulting Clematis seedlings in a controlled environment.

'EVIpo024' was selected by Raymond J. Evison and Mogens N. Olesen in their Clematis development program in Domarie Vineries Les Sauvagees, St. Sampsons, Guernsey, Channel Islands, United Kingdom in April 1998.

Asexual reproduction of 'EVIpo024' by cuttings was first done by Raymond J. Evison and Mogens N. Olesen in Domarie Vineries Les Sauvagees, St. Sampsons, Guernsey, Channel Islands, United Kingdom in May 1998. This initial and subsequent propagations have demonstrated that the characteristics of 'EVIpo024' are true to type and are transmitted from one generation to the next.

BRIEF DESCRIPTION OF THE DRAWING

The accompanying color illustration show as true as is reasonably possible to obtain in color photographs of this type:

FIG. 1.1 Stem and Juvenile Foliage;

FIG. 1.2 Entire leaf;

FIG. 1.3 Flower bud, flower upon opening Flower buds attached to stem, And leaves;

FIG. 1.4 Open flower, upper side;

FIG. 1.5 Open flower, lower side.

DETAILED DESCRIPTION OF THE VARIETY

The following is a detailed description of 'EVIpo024', as observed in its growth throughout the flowering period in glasshouses at Domarie Vineries Les Sauvagees, St. Sampsons, Guernsey, Channel Islands, United Kingdom. Plants are 2 years of age. Certain phenotypical characteristics of the variety may vary under different environmental, cultural, agronomic, seasonal, and climatic conditions. Color references are made using The Royal Horticultural Society (London, England) Colour Chart, 2001.

For a comparison, the nearest existing Clematis variety is cl. 'EVIfour', a patented variety described and illustrated in U.S. Plant Pat. No. 9,299 and issued on Oct. 28, 1994. Chart 1 details several physical characteristics of 'EVIpo024' and 'EVIfour'.

CHART 1

| | 'EVIpo024' | 'EVIfour' |
|---|---|---|
| Growth. | Compact: seasons growth normally 1.0M | Average: seasons growth normally greater than 2.0M |
| Flower size. | Small 90–130 mm diameter. | Medium 120–160 mm diameter. |
| Ability to flower. | Improved flowering as a young plant. | |
| Tepal arrangement. | Tepals overlap giving very "full" flower appearance. | Tepals only touch or overlap slightly-flower appears more gappy. |
| Bud Color. | Green RHS 138C | Green with red tones. |
| Internode length. | Very small 40–70 mm | Medium 120–160 mm. |

Parentage information:
*Pollen parent.*—H. F. Young.
*Seed parent.*—Burma Star.

FLOWER AND FLOWER BUD

Blooming habit: May through September.
Flower bud:
*Size.*—20–35 mm in length. Bud diameter is 12 to 15 mm.
*Bud form.*—Ovate.
*Bud color.*—RHS 138C of the Green Color Group at ¼ opening.
*Tepals.*—RHS N79C of the Violet Color Group.
*Peduncle.*—Surface: Smooth. Length: 30 mm–60 mm average length. Color: Green Group 137C. Strength: Strong.
*Receptacle.*—Surface: None.
*Borne.*—In clusters. Compound Cymes. Some early season flowers may be borne singly.
Flower bloom:
*Size.*—90 to 130 mm diameter. Depth is 5 to 10 mm.
*Lastingness.*—On the plant, flowers last 7 to 12 days.
*Form.*—Upon opening, flat to concave with tepals normally straight, occasionally reflexing.
*Color.*—Upon opening, the upper surface is RHS N79D of the Purple Color Group. Upon opening, the reverse side is RHS N79D of the Purple Color Group. With green (RHS 137C) central bar. After opening, the upper surface is RHS 79D of the Purple Color Group. After opening, the reverse surface is RHS N79D of the Purple Color Group. The base of the tepals is RHS 79D of the Violet Group.
*Variations.*—None.
*Fragrance.*—Very light floral.
Tepals:
*Tepal count.*—Double. Average range: 6–8.
*Shape.*—Individual tepal shape is elliptic-obovate. Base is rounded. Apex is acute.
*Cross section.*—Flat.
*Undulation of margin.*—Weak.
*Margin.*—Entire.
*Size.*—50 to 60 mm long. 25 to 30 mm wide.
*Tepal apex.*—Narrowly acute.
*Recurvature of tip.*—Outer sepals occasionally recurved.
*Persistence.*—Tepals drop away cleanly from plant.
*Arrangement.*—Tepals are arranged regularly.

Reproductive organs:
*Pollen.*—Color: Yellow Group 2D.
*Anthers.*—Size: 5–7 mm in length. Color: Yellow Group 2D with Red Purple Group 72A longitudinal bar.
*Filaments.*—Size: 10–12 mm in length. Color: Purple Group 79D.
*Stigmas.*—As flower ages, the stigma may protrude slightly from between the anthers. Stigma color Yellow Group 2D.
*Pistils.*—35 to 45 in quantity.

PLANT

Plant form: Climbing and spreading.
Plant growth: Very compact.
Height: Seasons growth attains 1.0 meters.
Spread: Typically 0.3 to 0.7 meter.
Hardiness: Trials to date show the variety is cold tolerant to USDA Cold Hardiness Zones 4–9.
Stems:
*Size.*—Stem diameter is 2 mm. From base of plant to flower, 0.7 to 1 meter.
*Color.*—Older wood: Greyed Red 178B. After several seasons turning to a Greyed Orange Group 165C.
*Internodes.*—Cylindrical. Length: 40–70 mm.
*Petioles.*—Incidence: Moderate. Size: Average length: 30–60 mm. Petiolule: 15–50 mm. Color: Greyed Purple Group 187A. Clasping: By winding leaf petiolus.
*Bark.*—Young wood: Smooth. Older wood: Smooth.
Plant foliage: Deciduous 3 ovate leaflets arranged in pinnate form.
*Terminal leaflet size.*—Small; 40 to 50 mm (l)×20–30 mm (w).
*Compound leaf size.*—150 mm (l)×100 mm (w).
*Abundance.*—Average.
*Color.*—Top: Green. RHS 137C of the Green Color Group with intonations of Red-Purple Group 60A. Bottom: RHS 137 C of the Green Color Group. New growth: Green. RHS 137C.
Plant leaves and leaflets:
*Stipules.*—Absent.
*Petiole.*—Length: 30×60 mm. Underneath: Without prickles.
*Leaf edge.*—Terminal leaflet margin is entire.
*Shape.*—Base of leaflet: Rounded occasionally cordate. Apex of leaflet: Acute.
*Texture.*—Upper side: Glabrous with matte surface. Lower side: Ribbed with glossy finish.
*Thickness.*—Thin.
*Glossiness.*—Upper side: Glabrous with matte surface. Lower side: Ribbed with glossy finish.
Disease resistance: Subject to any disease that normally attacks the species, however the variety is more tolerant to botrytis than some cultivars.

We claim:

1. A new and distinct variety of Clematis plant named 'EVIpo024', as illustrated and described herein as a distinct and novel clematis variety due to its abundant purple flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

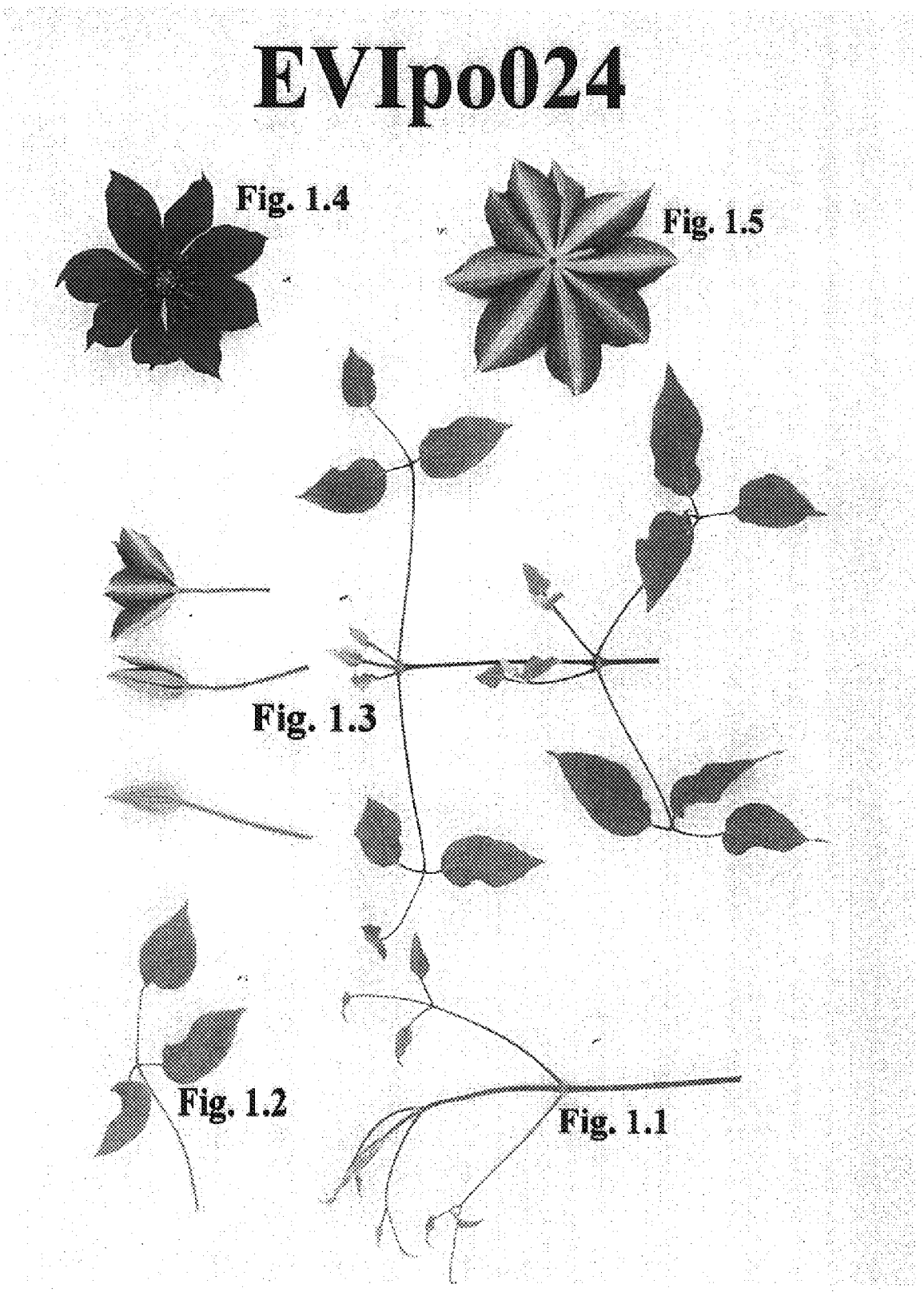
EVIpo024
Fig. 1.4
Fig. 1.5
Fig. 1.3
Fig. 1.2
Fig. 1.1